United States Patent [19]

van der Klugt

[11] Patent Number: 5,396,978
[45] Date of Patent: Mar. 14, 1995

[54] APPARATUS FOR ATTACHING ELASTIC AT AN ANGLE

[75] Inventor: Walter P. H. L. van der Klugt, Cincinnati, Ohio

[73] Assignee: The Procter & Gamble Company, Cincinnati, Ohio

[21] Appl. No.: 104,300

[22] Filed: Aug. 9, 1993

[51] Int. Cl.⁶ .......................................... B65G 47/24
[52] U.S. Cl. .................................................. 198/377
[58] Field of Search ............................... 198/377, 378

[56] References Cited

U.S. PATENT DOCUMENTS

| | | | |
|---|---|---|---|
| 2,074,929 | 3/1937 | Martin | 112/2 |
| 3,097,733 | 7/1962 | Frydryk | 198/33 |
| 3,269,516 | 8/1966 | Lucas | 198/33 |
| 3,618,838 | 11/1971 | Schieven et al. | 226/95 |
| 3,628,654 | 12/1971 | Haracz | 198/179 |
| 3,783,991 | 1/1974 | McCahon et al. | 198/33 |
| 3,952,874 | 4/1976 | Owen | 198/377 |
| 4,087,308 | 5/1978 | Baugher et al. | 156/405 R |
| 4,227,952 | 10/1980 | Sabee | 156/164 |
| 4,574,022 | 3/1986 | Johnson et al. | 198/377 |
| 4,920,904 | 5/1990 | Frye | 112/262.1 |
| 5,018,462 | 5/1991 | Brocklehurst | 112/121.12 |
| 5,104,116 | 4/1992 | Pohjola | 271/185 |
| 5,224,405 | 7/1993 | Pohjola | 83/24 |

Primary Examiner—Joseph E. Valenza
Attorney, Agent, or Firm—Marshall, O'Toole, Gerstein, Murray & Borun

[57] ABSTRACT

This disclosure relates to a machine which receives a strip or strips of material, rotates the strip or strips, and transfers the strip or strips to sheet material. The machine comprises a plurality of tables including first and second adjacent tables, and a conveyor connected to the tables for moving the tables sequentially through first and second zones and through at least one turning zone which is between the first and second zones, the adjacent tables when in the first zone having an initial orientation and having adjacent edges which are closely spaced. The turning zone includes a mechanism for moving the tables along an arcuate path and thereby separating the adjacent edges, and another mechanism for rotating the tables to a second orientation while the adjacent edges are separated, and the adjacent tables when in the second zone have the second orientation and have adjacent edges which are closely spaced. The disclosure also relates to a method of moving the tables through the zones and rotating the tables while moving the tables along an arcuate path.

11 Claims, 5 Drawing Sheets

APPARATUS FOR ATTACHING ELASTIC AT AN ANGLE

FIELD AND BACKGROUND OF THE INVENTION

This invention relates to machines and methods for manufacturing articles made up of multiple layers of materials and/or strips.

Numerous machines are known in the prior art for separately moving lines of sheets and/or strips to an assembly location and attaching the sheets and/or strips to produce an assembled article. For example, the S. R. Schleven U.S. Pat. No. 3,618,838 describes a conveyor mechanism for carrying separate layers of webs to an assembly area and forming a multilayered structure. The conveyor is formed by a series of trucks which form a rigid support surface, and the layers are held by vacuum on the trucks.

In some instances the webs or strips initially extend in the direction of the line of movement of the conveyor, and it is desirable to rotate segments of a selected web or strip so that the segments extend at an angle to the initial line of movement. For example, the M. B. Lucas U.S. Pat. No. 3,269,516 (assigned to The Procter & Gamble Company), and the prior art discussed in this patent, disclose machines for manufacturing disposable diaper pads formed from flexible sheet material. During the manufacture, each diaper pad is rotated through an angle by a turning mechanism. The M. B. Lucas patent discloses a machine including a series of turning heads that are moved by a chain conveyor, each turning head carrying a pad, and a turning mechanism rotates the turning head. Since, as shown by the drawings of the Lucas patent, adjacent turning heads are spaced a substantial distance apart, the heads may be rotated by the turning mechanism without interference between adjacent heads.

In some instances, however, an essentially continuous rigid support surface formed by a series of closely adjacent plates or heads is desired. In this situation, turning of a head would be obstructed by a closely adjacent head. To overcome this problem, some machines of this character have been provided with mechanisms for shifting a head out of the plane of the adjacent heads, turning the head while so shifted and then returning the head to the plane of the adjacent heads. Such an arrangement, however, requires rather complex mechanisms for both shifting and turning a head, and this is particularly true in a machine that also has a vacuum arrangement for holding a strip or sheet on the head.

It is therefore a general object of the present invention to provide an improved machine and method for assembling sheets and/or strips, including improved means for turning tables that carry sheets or strips.

SUMMARY OF THE INVENTION

A machine in accordance with the present invention comprises a plurality of tables, each of the tables having a support surface and edges around the support surface. A conveying mechanism is connected to each of the tables and, during operation, moves the tables along a track which includes a receiving straight portion, an assembly straight portion, and first and second curved portions which connect the ends of the two straight portions. At each of the two straight portions, the edges of adjacent tables are closely adjacent each other so that the tables form an essentially continuous bed. At the two curved portions, the tables swing through arcs which cause the adjacent edges to separate, and mechanisms are provided for turning the tables while the edges are so separated and thus do not interfere. The adjacent edges of the tables are configured such that the tables form substantially continuous beds at both straight portions, before and after turning at the curved portions.

A method in accordance with the invention comprises the steps of moving a plurality of tables along a first straight track portion, with the tables having a first orientation and the edges of adjacent tables being closely adjacent each other; moving the tables along a first curved track portion to separate the adjacent edges and turning the tables to a second orientation; moving the tables along a second straight track portion with the tables having the second orientation and the edges of adjacent tables being closely adjacent each other; moving the tables along a second curved track portion to separate the adjacent edges and turning the tables to the first orientation; and returning the tables to the first straight track portion.

BRIEF DESCRIPTION OF THE DRAWINGS

The invention will be better understood from the following detailed description taken in conjunction with the accompanying figures of the drawings, wherein.

DETAILED DESCRIPTION OF THE DRAWINGS

While the invention is illustrated and described in connection with the manufacture of disposable diapers, it should be apparent that the invention also has utility in other fields. Such diapers frequently include an absorbent pad and strips fastened to the pad at locations such as along the leg openings and/or along the waist edges, and a machine and method in accordance with this invention receives the strips and attaches the strips to the diaper pads.

Figures 1, 2, 8:
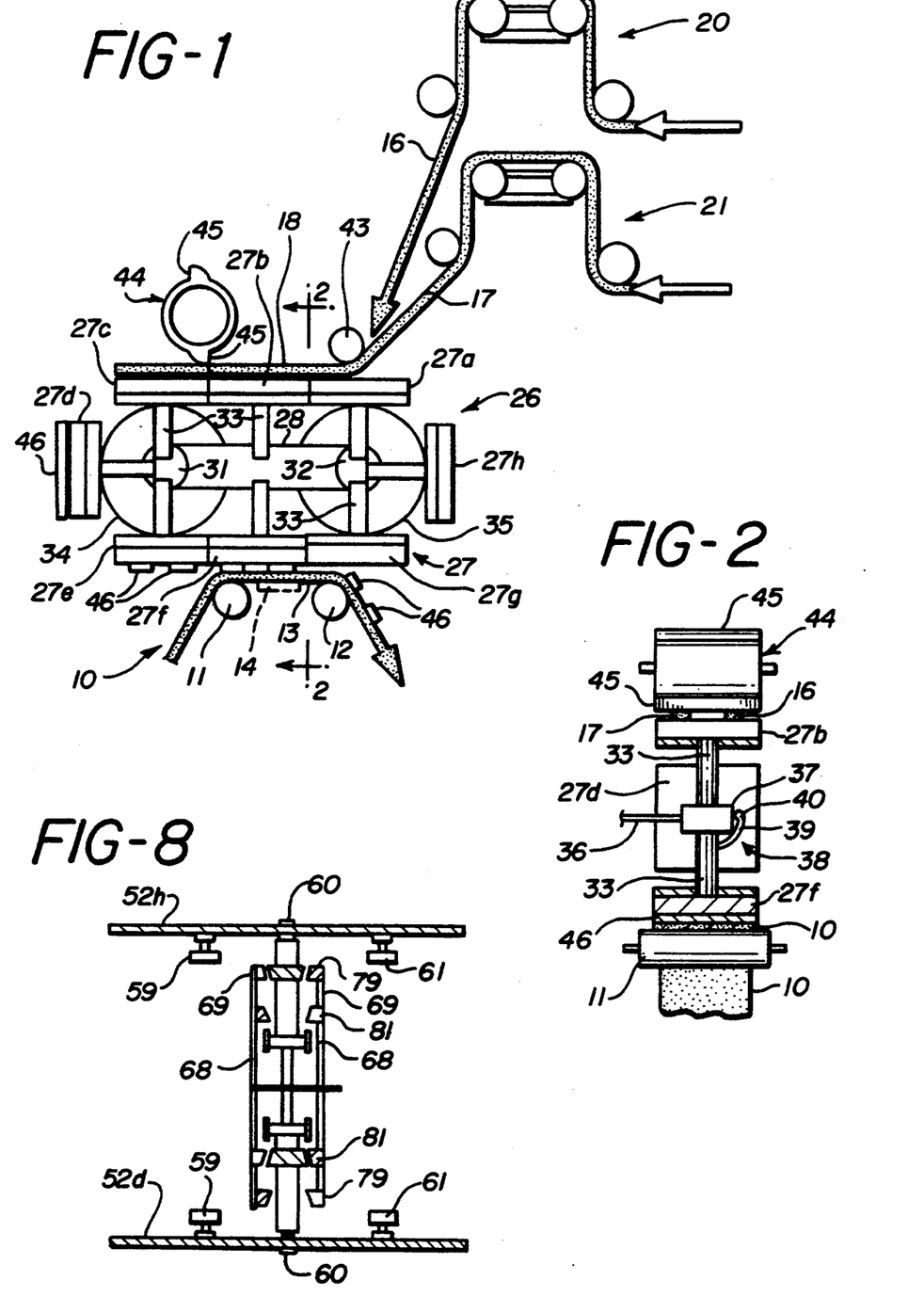
FIG. 1 is a schematic view of a machine constructed in accordance with the invention.
FIG. 2 is a view taken along the line 2—2 of FIG. 1.
FIG. 8 is a view taken on the line 8—8 of FIG. 4.

With reference first to FIGS. 1 and 2, a long length of pad material 10 is fed from a supply roll (not shown) over two assembly rollers 11 and 12 to a take-up roll (not shown). A portion 13 of the material 10 extends in a straight line or path at a transfer zone between the two rollers 11 and 12, and, if needed, a stiff support 14 may be provided underneath the straight portion 13.

Two narrow continuous strips 16 and 17 (which may be the same or different) to be assembled with or attached to the material 10 are fed from separate supply rolls (not shown) to separate tracking mechanisms 20 and 21. The strips 16 and 17 may, in this specific example, be impervious to air and each strip may have an adhesive layer on its upper side 18.

The pad material 10, the two strips 16 and 17 and the tracking mechanisms 20 and 21 may have conventional constructions.

A machine 26, constructed in accordance with the present invention and illustrated schematically in FIGS. 1 and 2, receives the two strips 16 and 17, cuts the strips into discrete lengths, and fastens the cut lengths to the pad material 10. The machine 26 comprises a plurality of tables or transport trays 27 (in this specific example there are eight tables designated 27a to 27h) which are moved, during operation of the machine, by a conveyor 28. The conveyor 28 comprises, for example, an endless chain or belt which extends around two rotatable rollers 31 and 32 and is connected by eight evenly spaced support shafts 33 to the tables 27. The tables 27 and the shafts 33 swing in semicircular arcs around the rollers 31 and 32. Semicircular surfaces 34 and 35 may (although not necessarily) be provided for the undersides of the tables to ride on, and in the present specific example, the surfaces 34 and 35 are formed by two drums that are concentric with the rollers 31 and 32.

With reference to FIG. 2, a vacuum system is connected by a tube 36 to a chamber 37 at the center of the machine, and the chamber 37 is connected to the tables 27 which are at the positions of the tables 27b, 27c, 27d, 27e and 27f, the three tables 27g, 27h and 27a being free of the vacuum. The vacuum connection may be made, for example, by a passage through the shafts 33 to the chamber 37. The purpose of the vacuum is to hold cut lengths or segments of the strips 16 and 17 in place on the tables.

The machine further includes turning mechanisms 38 (FIG. 2) at the locations of each of the two tables 27d and 27h for rotating or turning the tables which are moving around the arcuate surfaces 34 and 35. In this example, arcuate cams 39 are mounted on the machine frame adjacent the outer surfaces of the drums 34 and 35, and cam followers 40 are mounted on the undersides of the tables 27. At both turning ends of the machine, the tables moving around the drums 34 and 35 are turned through an angle of 90°.

Each of the eight tables 27 has outer edges which are square (see the table 27d in FIG. 2), and the tables are spaced apart and attached to the conveyor such that the three tables 27a, 27b and 27c have their adjacent edges closely adjacent each other and form an application zone. The adjacent edges extend transversely of the direction of movement, and the three tables 27a, 27b and 27c form an essentially flat, continuous bed. Similarly, the three tables 27e, 27f and 27g have their adjacent edges closely adjacent one another and these tables also form an essentially flat, continuous bed at a transfer zone.

The two continuous strips 16 and 17 (FIG. 1) extend from the feed mechanisms 20 and 21 to and under an application roller 43, the two strips 16 and 17 extending in side-by-side relation in the direction of movement (toward the left as seen in FIG. 1) of the three tables 27a, 27b and 27c, and the strips move at the same speed as the tables. The application roller 43 lays the strips down on the table 27a, and the vacuum applied to the tables 27b and 27c holds the strips in place. A rotating cylindrical knife 44 having two blades 45 is mounted over the tables 27b and 27c, and the rotation of the knife 44 is timed with the movement of the tables such that the blades 45 engage and sever the two strips 16 and 17 at the lines where the adjacent edges of the tables 27b and 27c adjoin. Thus the three tables 27a, 27b and 27c may be considered a pick-up or application zone of the machine where the machine receives the two strips 16 and 17, and the blades 45 sever the continuous strips 16 and 17 into discrete lengths or segments 46.

The segments 46 of the strips on the table 27c have their long dimensions extending in the direction of movement of the tables. As the table 27d moves around the turning surface 34, its outer edges move away from the adjacent tables 27c and 27e because the shaft 33 is connected to the center of the table and the outer edges (the edges that are spaced apart in the direction of movement of the conveyor 28, or, in other words, the two edges which are perpendicular to the initial direction of movement) swing through a greater arc than that of the center of the table. The turning mechanism 38 turns the table 27d through an angle of 90° as it moves around the surface 34, with the result that the strips 46 are turned to extend transversely of the direction of movement of the tables as shown by the two strips 46 on the table 27e.

The pad 10 moves over the two rollers 11 and 12 closely adjacent the table 27f and the rate of movement of the pad 10 equals that of the tables. The previously mentioned adhesive on the outer sides of the strips 16 and 17 is pressed firmly against the upper surface of the pad 10, and when the vacuum on the table 27g is removed, the segments 46 of the strips are carried away from the machine by the pad. If desired to increase the adhesion between the pad and the segments, a bumper roll may be provided to press the pad 10 against the table 27f. Another machine, not illustrated, may receive the assembled pad and strip segments and cut the pad into separate diapers having two strip segments 46 per diaper.

Another turning mechanism 38 is also provided at the returning end of the machine at the location of the table 27h to rotate the table 27h in the opposite direction through an angle of 90° and return it to the initial orientation of the tables 27a, 27b and 27c.

Figure 3:
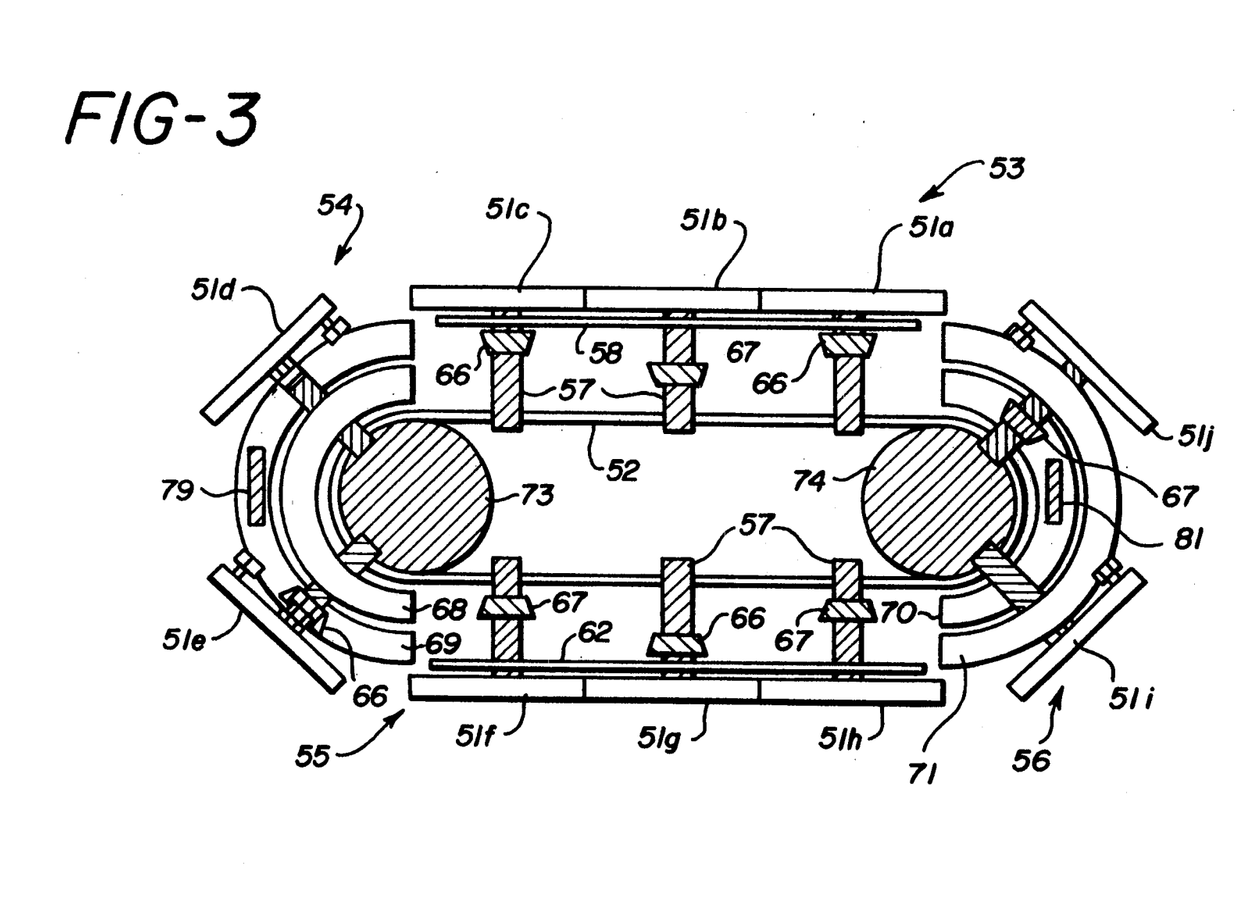
FIG. 3 is a view of another embodiment of the machine, containing ten turnable tables.

FIGS. 3 to 8 illustrate machines similar to that of FIGS. 1 and 2 and show a different turning mechanism. FIG. 3 shows a machine having ten tables 52a, 51b, ... 51j, and FIGS. 4 to 8 show a machine having eight tables 52a, 52b, ... 52h. These two machines are otherwise similar and are described together, and the same reference numbers are used for corresponding parts.

Figure 4:
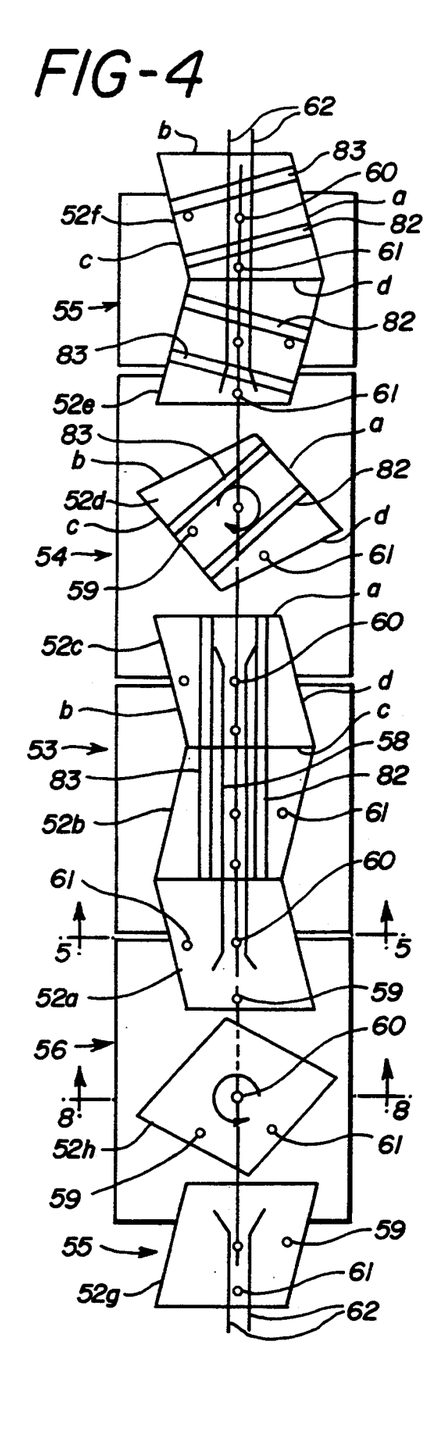
FIG. 4 is a flat schematic layout of a machine similar to that shown in FIG. 3 but containing eight turnable tables.
Figure 5:
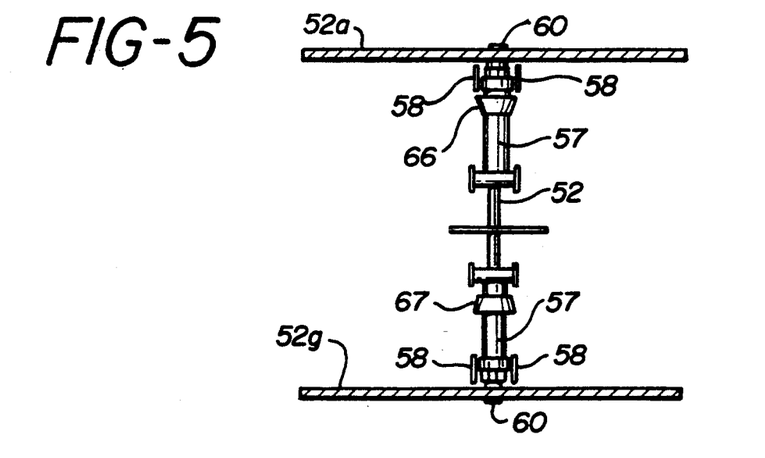
FIG. 5 is a view taken on the line 5—5 of FIG. 4.

The machine shown in FIG. 3 shows the ten tables 51a to 51j attached to and moved by a chain or belt conveyor 52. The three tables 51a to 51c are at an application zone 53 of the machine, the two tables 51d and 51e are at a turning zone 54, the three tables 51f to 51h are at a transfer zone 55, and the two tables 51i and 51j are at a returning zone 56. Each of the tables is supported by a shaft 57 connected to the underside of the table at its center, and the interior end of each shaft 57 is attached to the conveyor 52. At the application zone 53 and at the transfer zone 55, guide rails 58 (see FIGS. 4 and 5) are provided on opposite sides of the shafts 57. Secured to the underside of each table and extending inwardly are two guide pins 59 and 61; when in the application zone 53, the guide pins 59 are straight behind the pivot axes 60 (see FIG. 4) of the tables and are between the guide rails 58 and the second guide pins 61 are spaced to one side of the guide rails; and when in the transfer zone 55, the pins 61 are straight behind the pivot axes 60 and are within a second pair of guide rails 62, whereas the pins 59 are to one side of the rails 62. As shown in FIG. 4, the pins 61 of the adjacent tables in the application as well as in the transfer zones are on alternating sides of the guide rails, because the tables are configured as mirror images.

With reference to FIG. 3, truncated cones 66 and 67 are attached to the shafts 57. The cones 66 associated with the alternate tables 52a, 51c, 51e, 51g and 51i are adjacent the outer ends of the shafts 57, and the cones 67 of the intermediate tables 51b, 51d, 51f, 51h and 51j are adjacent the interior ends of the shafts 57.

The turning zone 54 and the returning zone 56 include turning means for turning the tables as the tables move around arcuate paths. At the turning zone 54 are provided inner and outer arcuate turning tracks 68 and 69, and at the returning zone 56 are provided two similar inner and outer arcuate turning tracks 70 and 71. The conveyor 52 moves around the two turning drums 73 and 74, and the tracks 68 and 71 are concentric with the drums 73 and 74. The radially inner tracks 68 and 70 are aligned with the cones 67 and the radially outer tracks 69 and 71 are aligned with the cones 66. The two tracks 69 and 70 are on one lateral side of the shafts 57 and the two tracks 68 and 71 are on the other lateral side of the shafts 57.

Figure 6:
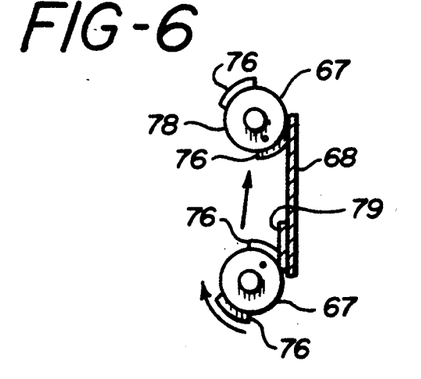
FIGS. 6 and 7 are views illustrating the operation of the machine shown in FIG. 4.
Figure 7:
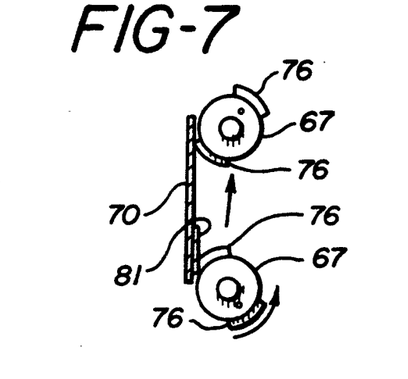

With reference to FIGS. 6 and 7, each of the cones 67 includes arcuate gear segments 76 which are on opposite sides of the cones and are separated by open spaces 78. The cones 66 are similarly constructed. Further, attached to the arcuate turning tracks 68, 69, 70 and 71 are stationary gear segments 79 and 81.

With reference to FIG. 3, when the cone 67 of the table 51d, for example, moves past the gear segment 79 on the inner turning track 68, the gear teeth of one of the segments 76 engage segment 79 and the table 51d plus the shaft 57 connected to it are rotated through an angle around the pivot pin 60 of the table. The extent of angular movement is, of course, determined by the length of the gear segments 79 and 76. With reference to FIG. 6, the segment 76 engages the segment 79 as the cone 67 moves upwardly (as seen in FIG. 6) from the lower position to the upper position. After the cone 67 moves past the segment 79, the cone has rotated to the position shown at the upper part of FIG. 6 and remains in this position as the table moves into the transfer zone 55.

When the next adjacent table 51c moves through the turning section 54, the cone 66 moves past the segment 79 on the outer track 69, and the cone 66 plus the table 51c are turned as described above. However, since the track 69 is on the opposite side of the cone 66 from the track 68, the table 51c will be turned in the opposite direction from the table 51d. It will therefore be apparent that the successive adjacent tables are turned in opposite directions by reason of the tracks 68 and 69 being on opposite sides of the shafts 57 and by reason of the cones engaging the segments 79 of first one track 68 or 69 and then the other track 69 or 68.

With reference to the returning zone 56 (FIGS. 3 and 7), the two tracks 70 and 71 are similarly provided with gear segments 81, but in this instance the tracks rotate the tables back to their original orientations, in other words, to the initial orientations when at the zone 53.

The radially outer track 71 is on the opposite side of the shafts 57 from the outer track 69, and the inner track 70 is on the opposite side from the track 68. Consequently, the tables are turned in the opposite direction from the turning direction at the turning section 54.

With reference again to FIG. 4, this specific example shows eight tables 52a to 52h each having the shape of a parallelogram. Each of the three tables 52a 52b and 52c at the application zone 53 has leading and trailing edges a and c and side edges b and d. The edges a and b form an angle A and the edges b and c form an angle 180° minus A. In the present specific example, the two angles are substantially 75° and 105°. In the turning zone 54, the alternate tables 52b, 52d, etc. are turned clockwise through the angle A and the alternate tables 52a, 52c, etc. are turned counterclockwise through the angle A. The sides a and b of each table in the application zone 53 extend perpendicularly to the direction of movement of the conveyor 52, and the edges a and c of adjacent tables are closely adjacent each other as shown in FIGS. 3 and 4.

As the tables move around the drum 73 in the turning section 54, the edges a and c of each table move away or separate from the edges a and c of the adjacent tables, as shown in FIGS. 3 and 4. As a consequence, a table in the turning section 54 may be turned without interference by the adjacent tables.

After turning, the edges b and d of each table in the transfer zone 55 extend perpendicularly to the direction of movement of the conveyor 52, and the second guide pins 61 are located directly behind the pivot points 60. The shafts 57 and the pins 61 move between the guide rails 62 at the transfer zone 55, and the edges b and d of adjacent tables are closely adjacent each other.

At the returning section 56, the tables are again turned through the same angle but in the opposite direction to return the tables to the original orientation.

The machines shown in FIGS. 3 to 11 may also include mechanisms for laying strips of material on the tables in the application zone and for moving a diaper pad past the tables in the transfer zone, as well as vacuum mechanisms for holding the strips on the tables, as described in connection with FIG. 1. At both the application zone 53 and the transfer zone 55, the tables form a substantially continuous bed, and two strips 82 and 83 are laid down on the tables 52a, 52b and 52c in the application section, parallel to the direction of movement of the conveyor. The two continuous strips are cut at the end of the application zone. After turning in the section 54, the strips extend at an angle to the direction of movement of the conveyor, and the strips of adjacent tables in the transfer section form a V configuration.

Figure 12:
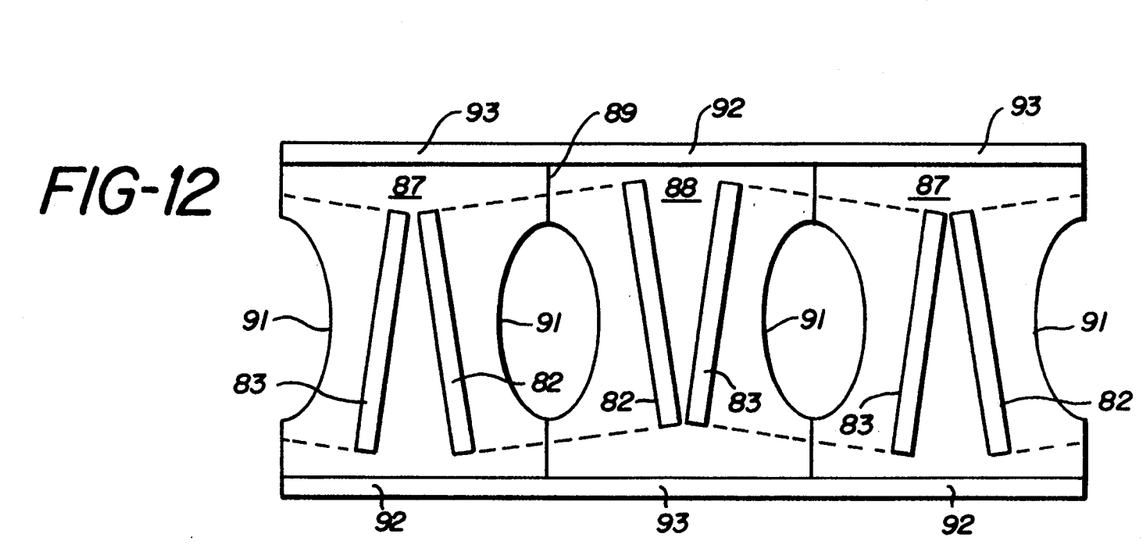
FIG. 12 illustrates a part of a diaper pad assembled using a machine illustrated in FIGS. 3 to 8.

FIG. 12 illustrates the strips after having been transferred to a strip 86 of diaper pad material by the machine illustrated in FIG. 3. Illustrated are two adjacent diapers 87 and 88 separated along a line 89, the diapers having leg openings 91, which may be already present or may be cut subsequently. The strips 82 and 83 of each table are transferred to the two adjacent diapers, as shown. The strips 82 and 83 are adjacent the leg openings 91, and each diaper further has a front edge strip 92 and a back edge strip 93.

The tables 51 of the machine shown in FIG. 3 may have the configuration and angular movement of the machine shown in FIGS. 4 to 8.

Figure 9:
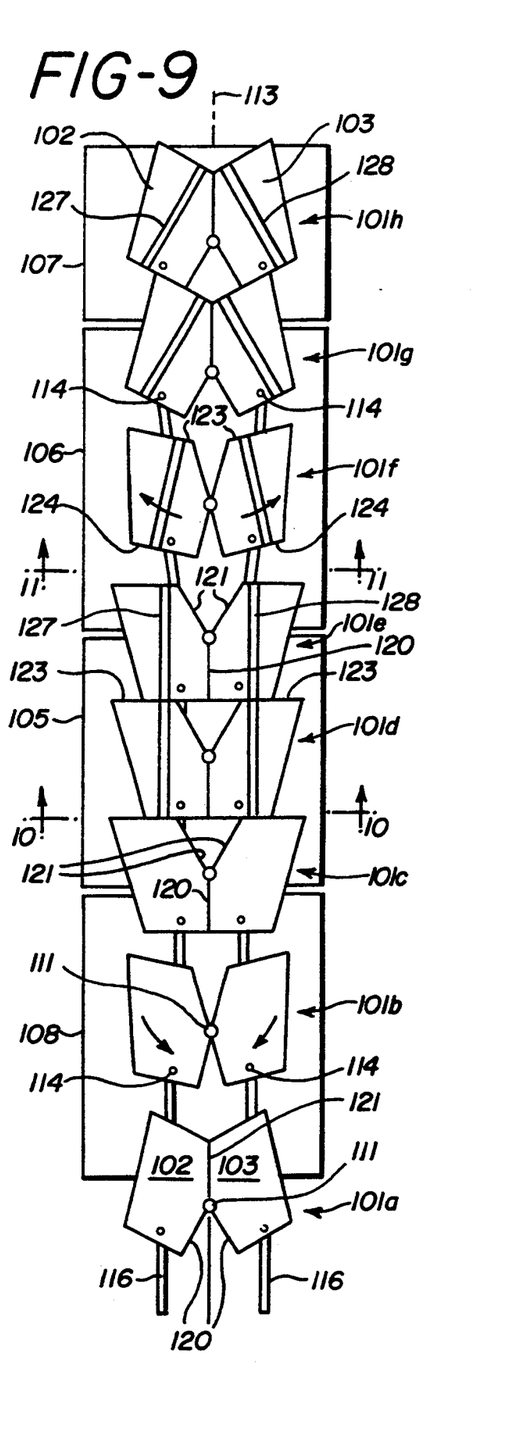
FIG. 9 is a flat schematic layout similar to FIG. 4 but illustrating an alternative embodiment.
Figure 10:
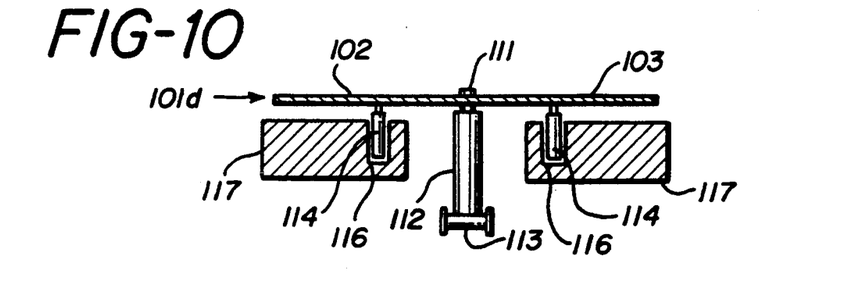
FIG. 10 is a view taken on the line 10—10 of FIG. 9.
Figure 11:
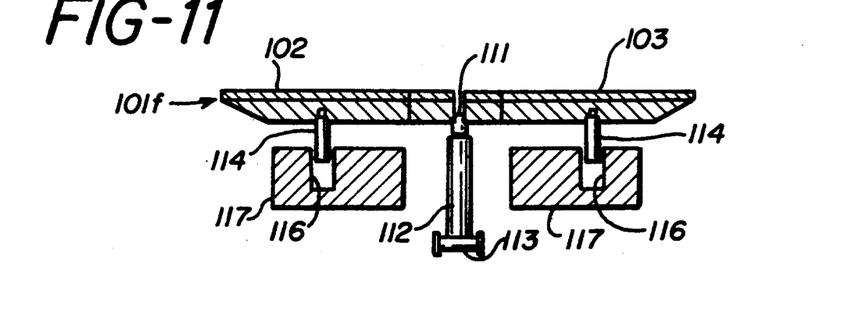
FIG. 11 is a view taken on the line 11—11 of FIG. 9.

FIGS. 9, 10 and 11 illustrate another embodiment of the invention wherein each table is formed by two side-by-side table sections. FIG. 9 schematically shows a flat layout of the tables but it should be kept in mind that the tables move on an endless conveyor as shown in FIGS. 1 to 3. The machine comprises, in this specific example, eight identical tables 101a to 101h, although more or fewer tables may be provided, and each table includes side-by-side sections 102 and 103. The tables 101c, 101d and 101e are at an application zone 105, the table 101f is at a turning zone 106, the tables 101g, 101h, and 101a are at a transfer zone 107, and the table 101b is at a returning zone 108. The tables are mounted and move upwardly (as seen in FIG. 9) through the stations 105, 106, 107, 108, 105, etc., as are the previously described tables.

The two sections 102 and 103 of each of the tables are connected to a pivot pin 111 which is at substantially the center of the table and is attached to a shaft 112 (FIGS. 10 and 11) that is attached to and is moved by a conveyor 113. Fastened to the underside of each section 102 and 103, at a location which is spaced behind, in the direction of movement, and laterally outwardly from the pivot pin 111, is a guide pin 114. The pins 114 are located in guide channels 116 formed in guide rails 117 (FIGS. 10 and 11) which extend underneath the tables through the four zones 105 to 108.

The guide channels 116 are spaced laterally on opposite sides of the pivot pins 111. In the application zone 105, the channels 116 are spaced a first distance from and are relatively close to the centerline 118 of the machine, the line 118 extending through the path of movement of the pivot pins 111. In the transfer zone 107, the channels 116 are spaced a second distance and are farther from the center line 118. In the turning zone 106, the spacing between the channels 116 widens and in the returning zone 108, the spacing narrows.

In each table, the two sections 102 and 103 have rearward adjacent edges 120 and forward adjacent edges 121. When in the application zone 105, the rearward adjacent edges 120 extend along the centerline 118 and the edges 120 of each table are close together, whereas the forward adjacent edges 121 are angled apart. When the table 101f moves through the turning zone 106, the increasing distance between the guide channels 116 causes the pins 114 to swing away from the centerline and the rearward portions of the table sections 102 and 103 to swing laterally outwardly. The table sections pivot to the orientations where the forward edges 121 are together and are on the centerline 118, whereas the rearward edges 120 are angled and spaced somewhat.

Of course, the angles of the edges 120 and 121 are correlated with the distances between the guide channels to move the edges 120 together in the application section and the edges 121 together in the transfer section.

Each of the table sections 102 and 103 further has a leading edge 123 and a trailing edge 124. In the application zone 105, all of the edges 123 and 124 are parallel and extend perpendicularly to the direction of movement of the conveyor; in the transfer zone 107, the leading and trailing edges of adjacent sections are again close to each other but extend at an angle to a perpendicular line. The angle of the edges 123 and 124 in the transfer zone 105 is, of course, equal to the angle through which the sections are pivoted in the turning and returning zones 106 and 108, and this angle is also related to the angles of the edges 120 and 121.

When in the application zone 105, the tables 101c, 101d and 101e form two essentially continuous flat beds which receive two parallel strips 127 and 128 that extend parallel to the direction of movement. When in the turning zone 106, the leading and trailing edges 123 and 124 become spaced apart, and the channels 116 (which act as cams) move the pins 114 (which are cam followers) and thereby pivot the sections and the strips to an angled orientation. In the transfer zone 107, the strips, which now form an angle with each other, are transferred to another article such as a diaper web 128 (see FIG. 13). After the transfer zone, the table sections are returned in the zone 108 to the initial orientation.

Figure 13:
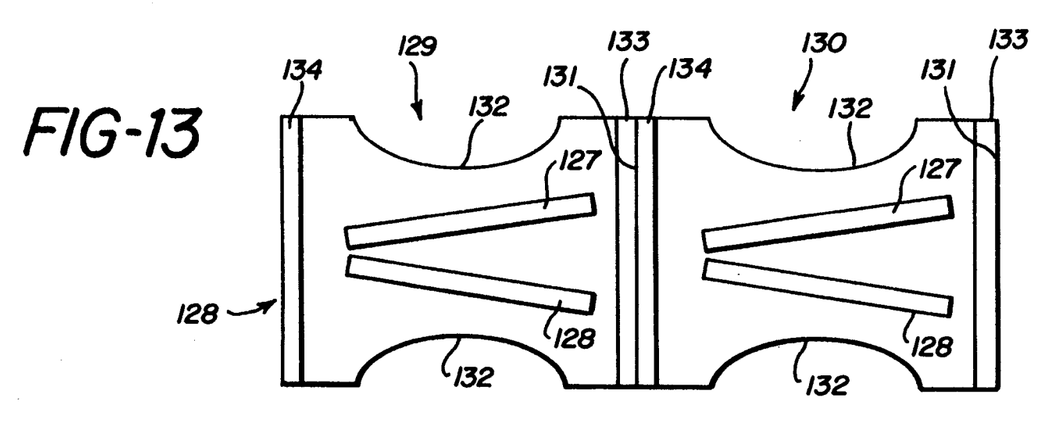
FIG. 13 is similar to FIG. 12 but shows a diaper pad assembled using the machine illustrated in FIG. 9.

FIG. 13 illustrates two diaper pads 129 and 130 of the web 128, the two pads 12 later being cut or separated along a line 131. Each pad includes leg openings 132 which may be cut prior or subsequent to the application of the strips 127 and 128. Each pad further includes front edge strips 133 and back edge strips 134.

It will be apparent from the foregoing that a novel and improved machine and method have been provided. The machine forms an essentially continuous bed which moves in one direction and receives at least one continuous strip that also moves in the same direction. The tables with the strips on them are turned to place the strips at an angle and then the angles strips are transferred to another article which is also moving in the one direction. By this arrangement, two continuous strips or articles moving in the same direction may, after being cut, be assembled at an angle to the other. The machine accomplishes the turning operation without the need for complex mechanisms because the turning operation takes place while the tables are naturally separated and are moving over a curved part of the machine. The movable tables or sections may be spaced sequentially in the direction of movement as shown, for example, in FIG. 4 or both sequentially and side by side as shown in FIG. 9.

The angles through which the adjacent tables are rotated are related to the angles of the edges of the adjacent tables (or the edges of the two sections of a single table as shown in FIG. 9), such that the edges closely adjoin each other both at the application zone and at the transfer zone. As a consequence, the tables form continuous beds which receive the strips or sheets from the delivery mechanisms 20 and 21 and from the delivery mechanism for the sheet 10. Even though the strips and sheet are delivered in a convenient fashion, in straight parallel lines which are parallel to the movement of the moving tables, they are assembled at angles to each other by turning the tables, and the turning is accomplished by moving the tables through arcs which separate adjacent edges of the tables. The adjacent edges swing through a greater radius than the pivot pins that carry the tables, and the greater radius separates the adjacent edges.

What is claimed is:

1. Apparatus comprising a purality of adjacent tables, each of said tables having a substantially flat support surface and outer edges around said support surface, conveyor means connected to said tables for moving said adjacent tables along a path of movement sequentially through first and second zones and through a turning zone which is between said first and second zones, said adjacent tables moving sequentially on said path of movement or both sequentially and side by side on said path of movement, said adjacent tables when in said first zone having an initial orientation and having adjacent edges which are closely spaced, said turning zone including first means for moving said tables along an arcuate path and thereby separating said adjacent edges, and second means for rotating said tables to a second orientation while said adjacent edges are separated, and said adjacent tables when in said second zone having said second orientation and having adjacent edges which are closely spaced, and said adjacent tables forming at least one essentially flat continuous bed in each of said first and second zones.

2. Apparatus as set forth in claim 1, wherein said adjacent edges in said first zone are different from said adjacent edges in said second zone.

3. Apparatus as set forth in claim 1, wherein said adjacent edges in said first zone are the same as said adjacent edges in said second zone.

4. Apparatus as set forth in claim 1, wherein said first means comprises a pivot shaft connecting said conveyor means to substantially the center of each of said tables and moving said table along said arcuate path.

5. Apparatus as set forth in claim 1, wherein said second means comprises cams and cam followers for rotating said tables.

6. Apparatus as set forth in claim 1, wherein said second means comprises gears for rotating said tables.

7. Apparatus as set forth in claim 1, wherein each of said tables comprises side-by-side first and second sections, each of said sections being rotated by said second means.

8. Apparatus as set forth in claim 7, wherein said sections are rotated in opposite directions by said second means.

9. Apparatus as set forth in claim 1, wherein said conveyor means further moves said tables sequentially through a second turning zone which is after said second zone and before said first zone, said second turning zone including third and fourth means similar respectively to said first and second means, said fourth means rotating said tables from said second orientation to said initial orientation.

10. Apparatus as set forth in claim 1, wherein said first table is rotated in one direction and said second table is rotated in the other direction.

11. Apparatus comprising a plurality of tables including at least first and second adjacent tables, each of said tables including a substantially flat support surface and outer edges around said support surface, conveyor means connected by pivot means to said tables for moving said tables sequentially through first and second zones and through a turning zone which is between said first and second zones, said adjacent tables when in said first zone having an initial orientation, said turning zone including first means for moving said tables along an arcuate path and second means for rotating said tables on said pivot means to a second orientation, and said adjacent tables when in said second zone having said second orientation, in each of said first and second zones, said outer edges of said adjacent tables closely adjoining each other and said support surfaces of said adjacent tables forming an essentially flat continuous bed.

* * * * *

UNITED STATES PATENT AND TRADEMARK OFFICE
CERTIFICATE OF CORRECTION

PATENT NO.   :   5,396,978
DATED        :   March 14, 1995
INVENTOR(S)  :   Walter P.H.L. van der Klugt It is certified that error appears in the above-identified patent and that said Letters Patent is hereby corrected as shown below:

Column 4, line 49, "tables 52a," should be --tables 51a,--.

Signed and Sealed this

Fifth Day of December, 1995

Attest:

BRUCE LEHMAN

*Attesting Officer*                *Commissioner of Patents and Trademarks*